United States Patent [19]

Chang et al.

[11] 4,177,202

[45] Dec. 4, 1979

[54] METHANATION OF SYNTHESIS GAS

[75] Inventors: Clarence D. Chang, Princeton; William H. Lang, Pennington, both of N.J.

[73] Assignee: Mobil Oil Corporation, New York, N.Y.

[21] Appl. No.: 918,878

[22] Filed: Jun. 26, 1978

Related U.S. Application Data

[63] Continuation-in-part of Ser. No. 775,133, Mar. 7, 1977, abandoned.

[51] Int. Cl.$^2$ ................................................ C07C 1/04
[52] U.S. Cl. ............................ 260/449 R; 260/449 M; 260/449.6 M; 260/449.6 R
[58] Field of Search ....................... 260/449 M, 449 R

[56] References Cited

U.S. PATENT DOCUMENTS

| | | | |
|---|---|---|---|
| 3,730,694 | 5/1973 | Wanderlich | 260/449 A X |
| 3,904,386 | 9/1975 | Graboski et al. | 260/449 M X |
| 3,927,997 | 12/1975 | Child et al. | 260/449 M |
| 3,927,998 | 12/1975 | Child et al. | 260/449 M |
| 3,927,999 | 12/1975 | Child et al. | 260/449 M |
| 3,928,000 | 12/1975 | Child et al. | 260/449 M X |
| 3,962,140 | 6/1976 | Alcorn et al. | 260/449 M X |

OTHER PUBLICATIONS

Schultz et al., Noble Metals, Molybdenum & Tungsten in Hydrocarbon Syntheses Report No. 6974, Bur. of Mines, 1967.
Wencke, Chem. Abs. 54 17022c, 1960.

Primary Examiner—Howard T. Mars
Attorney, Agent, or Firm—Charles A. Huggett; Michael G. Gilman; Carl D. Farnsworth

[57] ABSTRACT

Light gases rich in methane and ethane are produced from synthesis gas by contacting a CO reducing component of molybdena alone or in combination with an element selected from the group consisting of cobalt and vanadium distributed on a support of alumina or silica/alumina. The presence of hydrogen sulfide in the syngas feed enhances the activity and selectivity for the catalysts to produce ethane rich light gases.

1 Claim, No Drawings

METHANATION OF SYNTHESIS GAS

This application is a continuation-in-part of application Ser. No. 775,133, filed Mar. 7, 1977, and now abandoned, and contains information related to copending application Ser. No. 733,982, now U.S. Pat. No. 4,086,262 issued Apr. 25, 1978.

BACKGROUND OF THE INVENTION

Processes for the conversion of gaseous mixtures comprising hydrogen and carbon monoxide are known in the prior art. Also various processes may be employed for the preparation of such gases. Those of major importance depend either on the partial combustion of fuel with an oxygen containing gas or on the high temperature reaction of a selected fuel with steam, or on a combination of those two reactions. It is known that synthesis gas will undergo conversion reactions to form reduction products of carbon monoxide, such as hydrocarbons, at temperatures in the range of 300° F. to about 850° F., at pressures in the range of one atmosphere up to about 1000 atmospheres in the presence of a fairly wide variety of catalysts. The Fischer-Tropsch process for example, produces a range of liquid hydrocarbons, a portion of which have been used as relatively low octane gasoline materials. Catalyst employed in this process and some related processes include those based on metals and/or oxides of iron, cobalt, nickel, ruthenium, thorium, rhodium and osmium. On the other hand, the Fischer-Tropsch processing technology has been plagued with numerous problems such as deactivation of the catalyst with sulfur and catalyst regeneration problems. In addition it has been difficult to find and identify those conditions which produce liquid hydrocarbons boiling in the gasoline boiling range containing highly branched paraffins and substantial quantities of aromatic hydrocarbons required to produce high quality gasoline. A number of publications review the status of the Fischer-Tropsch synthesis art. None of these publications however provide a satisfactory answer for processing synthesis gas to hydrocarbons including those boiling in the gasoline boiling range where the catalyst is subjected to continuous or intermittent contact with sulfur.

SUMMARY OF THE INVENTION

The continually increasing use and need of natural gas for residential heating and industrial use, such as power generation, etc., emphasizes a need for a much greater supply of methane rich gases in the present and near future. This need focuses a renewed interest in processes for the catalytic hydrogenation of carbon monoxide to produce such gases and catalysts suitable for accomplishing that purpose in an economic manner.

It has now been found that synthesis gas comprising hydrogen and carbon monoxide, with or without the presence of sulfur such as by hydrogen sulfide, may be converted to hydrocarbons and particularly to gaseous hydrocarbons rich in methane. More importantly however is the finding that sulfur resistant carbon monoxide reducing catalyst may be relied upon to produce high BTU gaseous products rich in methane from syngas containing sulfur. Accordingly, the present invention in concerned with the catalytic conversion of syngas (synthesis gas comprising hydrogen and carbon monoxide) to form gaseous and liquid products including methane rich gases of high BTU value and liquid hydrocarbons employing a sulfur tolerant catalyst which may or may not be exposed to contact in sulfur in the syngas. More importantly however the present invention is directed to converting syngas comprising sulfur with a sulfur tolerant catalyst to methane rich gases wherein the activity and selectivity of the catalyst is improved by the presence of a sulfur compound such as hydrogen sulfide, carbon disulfide and/or carbonyl sulfide. In yet another embodiment, the present invention is concerned with increasing the yield of ethane in the methane rich gaseous product stream of the syngas conversion operation and the catalysts which are suitable for this purpose in the presence or absence of sulfur in the syngas. In a particular aspect the present invention is concerned with the use of a sulfur tolerant catalytic element selected from the group consisting of zirconium, thorium, hafnium, vanadium in admixture with a special class of crystalline zeolite providing a pore opening of at least 5 Angstroms, a silica to alumina ratio of at least 12 and a constraint index within the range of 1 to 12. The catalyst composition thus mentioned may be in admixture with a matrix material such as alumina, silica-alumina of relatively low acid activity or other matrix support material suitable for the purpose. In addition, the sulfur tolerant components above identified may be promoted with molybdenia. The sulfur tolerant catalytic element or carbon monoxide reducing component may be in the form of the metal, the oxide and/or the sulfide thereof or mixtures thereof which are employed alone with the special crystalline zeolite or in combination with molybdenia as a promoter to particularly influence the production of ethane.

The synthesis gas may be prepared from fossil fuels by any one of the methods known in the prior art including in situ gasification processes such as underground combustion of coal and petroleum deposits. The term fossil fuels is intended to include anthracite and bituminous coal, lignite, crude petroleum, shale oil, oil from tar sands, natural gas, as well as fuels derived by separation or transformation of these materials.

The synthesis gas produced from fossil fuels will often contain various impurities such as particulates, sulfur, and metal carbonyl compounds and will be characterized by a hydrogen to carbon oxides (carbon monoxide and carbon dioxide) ratio which will depend on the fossil fuel and the particular gasification technology utilized. In general, it has been essential heretofore to purify the raw synthesis gas for the removal of these impurities. It has now been found however that sulfur in the syngas (synthesis gas) need not be removed when the catalysts of this invention are employed to effect conversion of the synthesis gas. However, it may be desirable under some conditions to effect a partial removal of the sulfur and complete removal of other undesired contaminants. In the conversion operations of this invention, it is preferred to to adjust the hydrogen to carbon oxides volume ratio to be within the range of from 0.2 to about 6.0 and more usually adjusted to a 1-3/1 ratio prior to contact with the catalyst. The well known water gas shift reaction may be used to increase the hydrogen ratio if required or in the event of a hydrogen rich synthesis gas, it may be adjusted by the addition of carbon monoxide and/or carbon dioxide.

A synthesis feed gas comprising a mixture of hydrogen and carbon oxides obtained by the gasification of coal with steam normally produces hydrogen and carbon monoxide in a 1/1 ratio. This mixture can be used to perform the reaction:

$$2CO + 2H_2 \rightarrow CO_2 + CH_4$$

On the other hand, a ratio of hydrogen/carbon monoxide of 3/1 can be relied upon to perform the reaction:

$$3H_2 + CO \rightarrow CH_4 + H_2O$$

The water gas shift reaction is known as the following:

$$H_2O + CO \rightarrow CO_2 + H_2$$

Theoretically, reaction (2) and (3) performed simultaneously can be reduced to the combination of:

$$2H_2 + 2CO \rightarrow CH_4 + CO_2$$

In prior art studies above referred to, the most successful methanation catalyst, a nickel catalyst and a cobalt catalyst were both poisoned by sulfur. Also, these catalyst were not known as water gas shift catalysts. In one aspect, the present invention is concerned with the finding that the reactions of equations (2) and (3) above presented could be accomplished with a sulfur resistant carbon monoxide reduction catalyst. In another aspect, the present invention is concerned with the finding that the formation of methane in high yields can be produced with a sulfur resistant methanation catalyst and the catalyst activity and selectivity can be substantially unexpectedly improved by providing high concentrations of sulfur in the synthesis gas. More importantly, is the finding that sulfur increased the selectivity and conversion activity of the select group of carbon monoxide reducing catalyst herein identified for producing gases rich in methane. This beneficial effect increases with increases in sulfur concentration and is completely unexpected.

The heterogenous catalyst mixture of this invention is one comprising a metal oxide alone or in combination with a suitable matrix or it may comprise at least two components intimately mixed with one another and known and referred to as a sulfur insensitive or sulfur tolerant catalyst mixture. The sulfur tolerant component may or may not lose some activity in the presence of sulfur or its activity and selectivity for particular products may be substantially improved; but at least it will reactivate itself substantially completely simple by removing or reducing the presence of sulfur in the syngas feed. Thus, in the presence of this invention, it is particularly contemplated employing a catalyst mixture in which the carbon monoxide reducing component is selected from a class of inorganic substances that are substantially sulfur insensitive by having activity, and selectivity for the reduction of carbon monoxide in the presence of hydrogen to form hydrocarbons and in which the other component is a suitable support of matrix material, such as a faujasite zeolite or a zeolite selected from a particular class of crystalline aluminosilicate characterized by a pore dimension greater than about 5 Angstroms, a silica to alumina ratio greater than 12, and a constraint index in the range of 1 to 12. One class of crystalline zeolite so classified and identified herein is a class of crystalline zeolites represented by ZSM-5, ZSM-11, ZSM-12, ZSM-35, and ZSM-38.

A sulfur tolerant inorganic substance comprises one or more catalytic components which may lose some activity or be actively and selectively improved in the presence of sulfur and which will substantially reactivate itself by the removal of sulfur in the syngas feed. It is also contemplated that such catalyst compositions may be oxygen regenerated to remove deactivating deposits as a means for substantially restoring the activity and selectivity characteristics of the catalysts. On the other hand, it may be desirable to effect at least partial activity to the catalyst with a hydrogen rich atmosphere either by enriching the syngas feed with hydrogen or by a separate hydrogen contact of the catalyst.

The inorganic substance comprising elements selected from Groups IV B, V B, and VI B of the Periodic Table and consisting particularly of zirconium, hafnium, vanadium and throrium may be employed in amounts ranging from about 0.1% up to 80% by weight. Preferably the inorganic substance is less than 60% by weight of the active components of the catalyst mixture. Molybdenia may be present in the catalyst mixture in amounts within the range of 0 to 100 weight percent of the active components.

A number of known prior art Fischer-Tropsch synthesis catalysts other than the catalysts above identified such as nickel, cobalt and iron are poisoned by sulfur. Furthermore, the nickel and cobalt catalysts do not promote the well known shift reaction.

The catalysts referred to herein also utilize members of a special class of zeolites clearly distinguishable from faujasite zeolites and exhibit some unusual properties. These zeolites induce profound transformations of aliphatic hydrocarbons to aromatic hydrocarbons in commercially desirable yields and are generally highly effective in alkylation, isomerization, disproportion and other reactions involving aromatic hydrocarbons. Although they have unusually low alumina contents, high silica-alumina ratios, they are very active even with silica to alumina ratios exceeding 30.

An important characteristic of the crystal structure of this class of zeolites is that it provides constrained access to, and egress from, the intra-crystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred zeolites useful in type B catalysts in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful it is preferred to use zeolites having higher ratios of at least about 30. Such zeolites, after activation, acquire an intracrystalline sorption capacity for normal hexane which is greater than that for water, i.e., they exhibit "hydrophobic" properties. It is believed that this hydrophobic character is advantageous in the present invention.

The zeolites useful as catalysts in this invention freely sorb normal hexane and have a pore dimension greater than about 5 Angstroms. In addition, their structure may also provide constrained access to some larger molecules. It is sometimes possible to judge from a known crystal structure whether such constrained access exists. For example, if the only pore windows in a crystal are formed by 8-membered rings oxygen atoms, then access by molecules of larger cross-section than normal hexane is substantially excluded and the zeolite is not of the desired type. Zeolites with windows of 10-membered rings are preferred, although excessive puckering or pore blockage may render these zeolites substantially ineffective. Zeolites with windows of twelve-membered rings do not generally appear to offer sufficient constraint to produce the advantageous conversions desired in the instant invention, although structures can be conceived, due to pore blockage or other cause, that may be operative.

Rather than attempt to judge from crystal structure whether or not a zeolite possesses the necessary constrained access, a simple determination of the "constraint index" may be made by continuously passing a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of catalyst per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction Of 3-methylpentane remaining})}$$

The constraint index approximates the ratio of the cracking rate constants for the two hydrocarbons. Catalysts suitable for the present invention are those which employ a zeolite having a constraint index from 1.0 to 12.0. Constraint Index (CI) values for some typical zeolites including some not within the scope of this invention are:

| CAS | C.I. |
|---|---|
| Erionite | 38 |
| ZSM-5 | 8.3 |
| ZSM-11 | 8.7 |
| ZSM-35 | 6.0 |
| TMA Offretite | 3.7 |
| ZSM-38 | 2.0 |
| ZSM-12 | 2 |
| Beta | 0.6 |
| ZSM-4 | 0.5 |
| Acid Mordenite | 0.5 |
| REY | 0.4 |
| Amorphous Silica-alumina | 0.6 |

The above-described Constraint Index is an important and even critical, definition of those zeolites which are useful to catalyze the instant process. The very nature of this parameter and the recited technique by which it is determined, however, admit of the possibility that a given zeolite can be tested under somewhat different conditions and thereby have different constraint indexes. Constraint Index seems to vary somewhat with severity of operation (conversion). Therefore, it will be appreciated that it may be possible to so select test conditions to establish multiple constraint indexes for a particular given zeolite which may be both inside and outside the above defined range of 1 to 12.

Thus, it should be understood that the parameter and property "Constraint Index" as such value is used herein is an inclusive rather than an exclusive value. That is, a zeolite when tested by any combination of conditions within the testing definition set forth herein above to have a constraint index of 1 to 12 is intended to be included in the instant catalyst definition regardless that the same identical zeolite tested under other defined conditions may give a constraint index value outside of 1 to 12.

One special class of zeolites defined herein is exemplified by ZSM-5, ZSM-11, ZSM-12, ZSM-21, and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

U.S. application Ser. No. 358,192, filed May 7, 1973, the entire contents of which are incorporated herein by reference, describes a zeolite composition, and a method of making such, designated as ZSM-21 which is useful in this invention. Recent evidence has been adduced which suggests that this composition may be composed of at least two (2) different zeolites designated ZSM-35 and ZSM-38, one or both of which are the effective material insofar as the catalysis of this invention is concerned. Either or all of these zeolites is considered to be within the scope of this invention.

The subject of ZSM-35 is described in U.S. application Ser. No. 528,061 filed Nov. 29, 1974. The subject of ZSM-38 is described in U.S. application Ser. No. 528,060 filed Nov. 29, 1974.

The specific zeolites described, when prepared in the presence of organic cations, are substantially catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this special type zeolite; however, the presence of these cations does appear to favor the formation of this special type of zeolite. More generally, it is desirable to activate this type zeolite by base exchange with ammonium salts followed by calcination in air at about 1000° F. for from about 15 minutes to about 24 hours.

Natural zeolites may sometimes be converted to this type zeolite by various activation procedures and other treatments such as base exchange, steaming, alumina extraction and calcination, alone or in combinations.

Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12 and ZSM-21, with ZSM-5 particularly preferred.

The zeolites used as catalysts in this invention may be in the hydrogen form or they may be base exchanged or impregnated to contain ammonium or a metal cation complement. It is desirable to calcine the zeolite after base exchange. The metal cations that may be present include any of the cations of the metals of Groups I through VIII of the periodic table. However, in the case of Group IA metals, the cation content should in no case be so large as to substantially eliminate the activity of the zeolite for the catalysis being employed in the instant invention. For example, a completely sodium exchanged H-ZSM-5 appears to be largely inactive for shape selective conversions required in the present invention.

In a preferred aspect of this invention, the zeolites useful as catalysts herein are selected as those having a crystal framework density, in the dry hydrogen form, of not substantially below about 1.6 grams per cubic centimeter. It has been found that zeolites which satisfy all three of these criteria are most desired. Therefore, the preferred catalysts of this invention are those comprising zeolite having a constraint index as defined above of about 1 to 12, a silica to alumina ratio of at least about 12 and a dried crystal density of not substantially less than about 1.6 gram per cubic centimeter. The dry density for known structures may be calculated from the number of silicon plus aluminum atoms per 1000 cubic Angstroms, as given, e.g., on page 19 of the article on Zeolite Structure by W. M. Meier. This paper, the entire contents of which are incorporated herein by reference, is included in "Proceedings of the Conference Molecular Sieves, London, April, 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density of course must be associated with a relatively small amount of free space within the crystal, which might be expected to result in more stable structures. This free space, however, seems to be important as the locus of catalytic activity.

Crystal framework densities of some typical zeolites including some which are not within the purview of this invention are:

| Zeolite | Void Volume | Framework Density |
| --- | --- | --- |
| Ferrierite | 0.28 cc/cc | 1.76 g/cc |
| Mordenite | .28 | 1.7 |
| ZSM-5,-11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

The heterogeneous catalysts may be prepared in various ways. The two components may be separately prepared in the form of catalyst particles such as pellets or extrudates, for example, and simply mixed in the required proportions. The particle size of the individual component particles may be quite small, for example, from about 20 to about 150 microns, when intended for use in fluid bed operation; or they may be as large as up to about ½ inch for fixed bed operation. Or, the two components may be mixed as powders and formed into pellets or extrudate, each pellet containing both components in substantially the required proportions. Binders such as clays may be added to the mixture. Alternatively, the component that has catalytic activity for the reduction of carbon monoxide may be formed on the acidic crystalline aluminosilicate component by conventional means such as impregnation of that solid with salt solutions of the desired metals, followed by drying and calcination. Base exchange of the acidic crystalline aluminosilicate component also may be used in some selected cases to effect the introduction of part or all of the carbon monoxide reduction component. Other means for forming the intimate mixture may be used, such as: precipitation of the carbon monoxide reduction component in the presence of the acidic crystalline aluminosilicate; or electroless deposition of metal on the zeolite; or deposition of metal from the vapor phase. Various combinations of the above preparative methods will be obvious to those skilled in the art of catalyst preparation. It should be cautioned, however, to avoid techniques likely to reduce the crystallinity of the acidic crystalline aluminosilicate.

In the process of this invention, synthesis gas is contacted with the heterogeneous catalyst at a temperature in the range of from about 700° F. to about 1500° F., preferably from about 750° F. to about 950° F., at a pressure in the range of from about 10 to about 1000 atmospheres, preferably from about 20 to about 200 atmospheres, and at a volume hourly space velocity in the range of from about 500 to about 50,000 volumes of gas, at standard temperature and pressure per volume of catalyst, or equivalent contact time if a fluidized bed is used. The heterogeneous catalyst may be contained as a fixed bed, or a fluidized catalyst mass may be used. The product stream containing hydrocarbons, unreacted gases and steam may be cooled and the hydrocarbons recovered by any of the techniques known in the art, which techniques do not constitute part of this invention. The recovered hydrocarbons may be further separated by distillation or other means to recover one or more products such as high octane gasoline, methane, $C_2$–$C_4$ hydrocarbons, propane fuel, benzene, toluene, xylenes, or other aromatic hydrocarbons.

In a particularly preferred aspect, it is contemplated employing a fluid catalyst system comprising vanadium supported by an alumina binder or matrix material. The support material may also be an attrition resistant material such as a relatively inactive fluid cracking catalyst.

Materials suitable as a support or binder for the carbon monoxide reducing component includes alumina, a special class of crystalline zeolite represented by ZSM-5, a faujasite cracking catalyst, an amorphous silica-alumina cracking component of low activity and combination of these materials.

Methane containing varying amounts of ethane is produced from syngas employing a variety of sulfur tolerant catalyst as herein identified either in the presence or absence of substantial concentrations of hydrogen sulfide depending on the catalyst employed. Several of the catalysts employed actually achieved enhanced activity and/or methane selectivity when hydrogen sulfide is in the syngas feed. Presulfiding and oxygen activation of the sulfided catalyst may be practiced in this invention.

EXAMPLE 1

A sample of pure $ZrO_2$ was made by thermal decomposition of the oxalate thereof. Composite catalysts were made by ballmilling and pelleting.

Synthesis gas ($H_2/CO=1$) was reacted over zirconia and a zirconia-ZSM-5 crystalline zeolite composite catalyst at 1200 psig, 800° F. and 1.3–1.5 VHSV (gas at standard temperature and pressure) (based on $ZrO_2$) or 720–750 VHSV (based on total reaction volume). The effect of the ZSM-5 crystalline zeolite on the reaction product of zirconia appear to be similar to the effect observed of the zeolite upon a thoria catalyst. The principal effect observed is the reduction in methane formation. Some activity enhancement is evident and aromatics distribution appears to be similar to that observed when using a $ThO_2$/ZSM-5 catalyst.

WHSV is the weight of feed/weight of catalyst X time in hours.

VHSV is the volume of gas/volume of catalyst X time in hours.

STP is identified as standard temperature of 0° C. and 760 min. Hg.

The effect of $H_2S$ on $ZrO_2$/ZSM-5 catalyst activity was determined and reported in Table 1 below. The initial portion of the test (Run A) was run without $H_2S$ to establish a base case. The operating conditions were 600 psig, 800° F. and 1.3 WHSV (based on $ZrO_2$). After 20 hours on stream, about 3 wt.% of $H_2S$ was introduced on a continuous basis with the $H_2/CO$ syngas feed stream. A material balance was obtained after 26 hours continuous exposure to $H_2S$ (Run B). Catalytic activity, unexpectedly and quite surprisingly, was unimpaired. A slightly higher conversion observed in Run B appears to be attributable to a lower WHSV for the run. The main influence attributable to $H_2S$ appears to be to increase the methane yield (from 3.6% to about 11.2%) and to reduce aromatics formation. A significant amount of COS (carbonyl sulfide) was found in the effluent thus indicating that catalytic activity is also unaffected by this substance. The space velocity was then reduced to 0.26 WHSV (Run C). After an additional 24 hours on stream another material balance was made (Run C) which revealed a three-fold higher conversion and little change in selectivity. At the end of Run C, the $H_2S$ was removed from the feed and after an additional 22 hours on stream, a product analysis was made. This analysis showed a drop in methane make and recovery of the catalyst selectivity for producing aromatics. See Run D. The analysis also showed a lower conversion which can be partially accounted for in the use of a somewhat higher (WHSV) space velocity during the period to obtain a material balance. Catalyst aging may also be a contributing factor. It is even possible to rationalize that the $H_2S$ in the feed operates as a catalyst promoter. In any event the production of aromatics in Run D is higher than that obtained in Runs B and C.

TABLE 1

EFFECT OF $H_2S$ ON $ZrO_2$/HZSM-5 SYNGAS CONVERSION ACTIVITY
$H_2/CO = 1$, $H_2S \approx 3$ wt %

| Run | A | B | C | D |
|---|---|---|---|---|
| | | ←—$H_2S$ addition—→ | | |
| Reaction Conditions | | | | |
| Temperature, °F. | 800 | 800 | 800 | 800 |
| Pressure, psig | 600 | 600 | 600 | 600 |
| WHSV, $hr^{-1}$(a) | 1.3 | 1.0 | 0.26 | 0.34 |
| Time on Stream | 20 | 46 | 70 | 92 |
| Conversion, % | | | | |
| CO | 8.0 | 10.6 | 28.9 | 16.3 |
| $H_2$ | 8.8 | 10.7 | 36.0 | 13.0 |
| Total Effluent, wt % | | | | |
| Hydrocarbons | 2.7 | 3.7 | 13.1 | 6.8 |
| $H_2O$ | 1.8 | 1.1 | 2.8 | 0.2 |
| $CO_2$ | 3.6 | 8.2 | 14.1 | 9.1 |
| CO | 85.8 | 81.1 | 64.5 | 78.1 |
| $H_2$ | 6.1 | 5.8 | 5.3 | 5.8 |
| Other(b) | — | 0.1 | 0.2 | — |
| Hydrocarbons, wt % | | | | |
| Methane | 3.6 | 11.2 | 10.2 | 5.5 |
| Ethane | 7.9 | 8.5 | 11.7 | 12.4 |
| Ethylene | 0.2 | 0.2 | — | — |
| Propane | 12.6 | 19.6 | 13.6 | 12.1 |
| Propylene | 0.1 | 0.1 | — | — |
| i-Butane | 1.0 | 2.1 | 0.5 | 0.7 |
| n-Butane | 0.6 | 1.4 | 0.5 | 0.2 |
| Butenes | — | — | — | — |
| $C_5+$ PON | — | 0.2 | 0.1 | — |
| Aromatics | 74.0 | 56.7 | 63.4 | 69.1 |

(a)WHSV based on $ZrO_2$ component
(b)Mainly COS ($H_2S$-free basis)

EXAMPLE 2

The addition of ZSM-5 crystalline zeolite to a $ThO_2$ catalyst has enhanced activity, shifts the formed aromatics from $C_{11}+$ aromatics to primarily $C_{10}-$ aromatics and dramatically inhibits methane formation. It has also been observed that the addition of $Al_2O_3$ to a $ThO_2$/ZSM-5 catalyst combination improves the selectivity of the catalyst to form aromatics.

The data presented in Table 2 below demonstrate the effect of adding ZSM-5 crystalline zeolite on the activity and selectivity of a $ThO_2$ isosynthesis catalyst. Typical isosynthesis process conditions and yields are shown in Example 1 of Table 2. The process is normally operated at 4400 psig and yields isobutane as a major product. Some aromatics (mainly $C_{11}+$) are made as well as oxygenates. The high pressure of the operation is considered necessary to overcome a thermodynamic limitation on one of the primary steps in the reaction and not because of a kinetic limitation. The effect of reducing the pressure to 1200 psig is shown in Examples 2A and 2B of Table 2. It will be noted that a decrease in conversion is obtained. However, the most striking effect is the change in selectivity. Methane becomes the predominate product while isobutane yield is greatly reduced. In addition, it is observed that more olefins are formed. From Example 3, it is seen that changing the $ThO_2$/$Al_2O_3$ ratio from 5 to 4 has little effect on activity or selectivity. The liquid hydrocarbons produced in Examples 2 and 3 are mainly $C_{10}+$ hydrocarbons.

The effect of adding ZSM-5 to the catalyst of Example 3 is shown in Examples 4A and B of Table 2. The WHSV's were based on $ThO_2/Al_2O_3$, the component with highest density. Equivalent VHSV's were achieved by maintaining comparable reactor volumes in an effort to keep gas residence times at approximately equal levels. From these examples an enhancement in activity is observed with ZSM-5 addition as well as a dramatic change in selectivity.

In the presence of ZSM-5, methane levels are greatly reduced while LPG components increase. The predominate products are aromatics and they are largely trimethyl-benzenes as shown in Table 3 below. In Example 4 it is further observed that conversion levels drop (261 hours on stream) but aromatic yields are significantly higher.

TABLE 3-continued

| | AROMATICS DISTRIBUTION | | |
|---|---|---|---|
| Run Ident. | LPA 118A | LPA 97E | LPA 97G |
| Xylenes | 14.5 | 29.5 | 18.2 |
| Trimethylbenzenes | 29.9 | 56.6 | 62.9 |
| Other $A_9$ | 12.5 | 0.6 | 0.4 |
| $A_{10}$ | 28.4 | 21.0 | 17.1 |
| $A_{11}+$ | 11.4 | — | — |
| | 100.0 | 100.0 | 100.0 |

EXAMPLE 3

Table 4 below presents the data obtained on various $ThO_2$ (no alumina) catalysts. The activity of a pure $ThO_2$ catalyst at 1200 psig, 800° F. and 2.2 WHSV is shown in Example 5 of the table. The effect of added ZSM-5 is seen in Examples 6A and B. The main effects to be observed are enhanced conversion and reduced

TABLE 2

| EFFECT OF ZSM-5 ON $ThO_2/Al_2O_3$ IN SYNGAS CONVERSION ($H_2/CO = 1$) | | | | | | |
|---|---|---|---|---|---|---|
| Example | 1 | 2A | 2B | 3 | 4A | 4B |
| Run Ident. | Isosynthesis | LPA 117B | LPA 117C | LPA 118A | LPA 97E | LPA 97G |
| Catalyst Composition, wt. % | | | | | | |
| $ThO_2$ | 83 | 83 | 83 | 80 | 40 | 40 |
| $Al_2O_3$ | 17 | 17 | 17 | 20 | 10 | 10 |
| ZSM-5 | 0 | 0 | 0 | 0 | 50 | 50 |
| Reaction Conditions | | | | | | |
| Temperature, °F. | 797 | 800 | 800 | 800 | 800 | 800 |
| Pressure, psig | 4400 | 1200 | 1200 | 1200 | 1200 | 1200 |
| WHSV, $hr^{-1}$(a) | 0.33 | 0.38 | 1.4 | 1.3 | 1.4 | 1.4 |
| VHSV, $hr^{-1}$ | 600 | 240 | 900 | 840 | 900 | 900 |
| Time on stream, hr | 72 | 46 | 69 | 61 | 165 | 261 |
| Conversion, wt. % | | | | | | |
| CO | 73 | 18.2 | 11.8 | 11.2 | 21.2 | 18.0 |
| $H_2$ | 67 | 17.2 | 14.2 | 8.9 | 36.4 | 18.9 |
| Effluent Composition, wt. % | | | | | | |
| Hydrocarbons | | 3.4 | 2.3 | 2.6 | 5.8 | 5.9 |
| Oxygenates | | 0.6 | 0.7 | 0.5 | — | — |
| $H_2O$ | | 0.6 | 0.1 | 0.8 | 1.6 | 1.4 |
| $CO_2$ | | 13.7 | 8.9 | 7.1 | 14.8 | 10.8 |
| CO | | 76.3 | 82.3 | 82.9 | 73.5 | 76.5 |
| $H_2$ | | 5.5 | 5.7 | 6.1 | 4.3 | 5.4 |
| Hydrocarbons, wt. % | | | | | | |
| Methane | 15.0 | 47.1 | 41.0 | 47.5 | 1.8 | 5.2 |
| Ethane | 4.8 | 6.6 | 4.4 | 5.4 | 18.9 | 15.6 |
| Ethylene | — | 4.0 | 3.3 | 3.0 | 0.3 | 0.3 |
| Propane | 4.3 | 4.1 | 2.6 | 2.2 | 20.1 | 13.8 |
| Propylene | — | 4.8 | 3.9 | 3.1 | 0.3 | 0.2 |
| i-Butane | 46.6 | 2.7 | 1.7 | 1.0 | 3.7 | 2.0 |
| n-Butane | 5.2 | 0.2 | 0.1 | — | 2.2 | 0.2 |
| Butenes | 6.0 | 6.1 | 7.1 | 3.0 | — | — |
| $C_5+$ PON | 11.7 | 9.6 | 26.9 | 24.9 | 3.8 | 2.2 |
| Aromatics | 7.4(b) | 14.8 | 9.0 | 13.0(d) | 48.9(d) | 60.7 |
| Total $C_5+$ | 19.1 | 24.4(c) | 35.9(c) | 37.9(c) | 52.7 | 62.9 |
| Aromatics in $C_5+$ | 38.7 | 60.7 | 25.1 | 34.3 | 92.8 | 96.5 |

(a) WHSV based on $ThO_2/Al_2O_3$ component
(b) 79% $C_{11}+$
(c) 44-45% $C_{10}+$
(d) cf. Table 3 for aromatic distribution

TABLE 3

| | AROMATICS DISTRIBUTION | | |
|---|---|---|---|
| Run Ident. | LPA 118A | LPA 97E | LPA 97G |
| Catalyst Composition, wt % | | | |
| $ThO_2$ | 80 | 40 | 40 |
| $Al_2O_3$ | 20 | 10 | 10 |
| ZSM-5 | 0 | 50 | 50 |
| Aromatics in HC, wt % | 13.0 | 48.9 | 60.7 |
| Aromatics Distribution, wt % | | | |
| Benzene | — | 0.1 | — |
| Toluene | — | 1.7 | 1.3 |
| Ethylbenzene | 3.3 | 0.1 | 0.1 | methane make. However, the selectivity to aromatics is lower than that observed with the $Al_2O_3$ containing catalysts.

Combinations of $ThO_2$ with other zeolites, dealuminized erionite and REY crystalline zeolite, were listed for syngas conversion and reported in Examples 7 and 8 of Table 4. The erionite containing catalyst appears to also enhance conversion and depress methane formation. The hydrocarbons formed, however, are mainly low molecular weight hydrocarbons and non-aromatic. However, relatively high selectivity to ethylene and propylene is observed with the erionite containing catalyst. The REY component appears to contribute little more than a diluent when comparing Examples 5 and 8.

The inhibition of methane formation in the examples comprising a ZSM-5 crystalline zeolite and an erionite type of crystalline zeolite is a clear indication that an intermediate species in the reaction sequence is being intercepted since methane, once formed, is quite stable under the operating conditions employed.

in the interim, been exposed to air, the sample was found to be active after a simple pre-treatment with $H_2$ (LPA 125 A).

Sulfur (2% $H_2S$) was added to the syngas feed (LPA 125 B). The lowered space velocity was a result of experimental difficulties. However, the results clearly demonstrate the ability of the catalyst to function in the presence of sulfur. The effect of sulfur is mainly to

TABLE 4
ACTIVITY OF VARIOUS $ThO_2$ CATALYSTS FOR SYNGAS CONVERSION
($H_2/CO = 1$)

| Example | 5 | 6A | 6B | 7 | 8 |
|---|---|---|---|---|---|
| Run Ident. | LPA 78A | LPA 79C | LPA 79E | LPA 90A | LPA 80A |
| Catalyst Composition, wt. % | | | | | |
| $ThO_2$ | 100 | 50 | 50 | 50 | 50 |
| ZSM-5 | 0 | 50 | 50 | 0 | 0 |
| Other zeolite | 0 | 0 | 0 | 59 Erionite(b) | 50 REY |
| Reaction Conditions | | | | | |
| Temperature, °F. | 800 | 800 | 800 | 800 | 800 |
| Pressure, psig | 1200 | 1200 | 1200 | 1200 | 1200 |
| WHSV, $hr^{-1}$(a) | 2.2 | 3.4 | 0.36 | 3.7 | 2.5 |
| Time on Stream, hr. | 92 | 171 | 267 | 5 | 19 |
| Conversion, % | | | | | |
| CO | 5.3 | 11.8 | 57.2 | 11.3 | 5.3 |
| $H_2$ | 2.6 | 17.4 | 47.8 | 12.6 | 2.9 |
| Hydrocarbons, wt. % | | | | | |
| Methane | 41.0 | 17.3 | 11.3 | 13.7 | 42.8 |
| Ethane | 5.5 | 27.6 | 28.0 | 22.6 | 15.6 |
| Ethylene | 1.7 | 0.6 | 0.1 | 27.0 | 1.5 |
| Propane | 7.8 | 25.6 | 24.8 | 7.6 | 7.3 |
| Propylene | 3.1 | 1.3 | 0.2 | 13.3 | 3.6 |
| i-Butane | — | 12.1 | 4.3 | 3.7 | 3.1 |
| n-Butane | — | 6.6 | 2.7 | 1.1 | 0.2 |
| Butenes | 36.9 | — | — | 9.6 | 23.4 |
| $C_5+$ PON | 0.4 | 5.2 | 0.9 | 1.4 | 1.8 |
| Aromatics | — | 3.7 | 27.7 | — | 1.7 |
| Total $C_5+$ | 0.4 | 8.9 | 28.6 | 1.4 | 2.5 |

(a)WHSV based on $ThO_2$ component
(b)Dealuminized, $SiO_3/Al_2O_3 = 16.3$

Synthesis gas containing ~2% $H_2S$ has been converted to aromatic hydrocarbons over $ThO_2/Al_2O_3$/HZSM-5. The catalyst was found to be resistant to sulfur poisoning. This is demonstrated in the attached Table 5.

The catalyst was a sample of spent catalyst from Run LPA 97 which has previously accumulated 261 hours on stream. Despite the fact that the spent catalyst had, increase methane. In LPA 125 C, the S was removed, methane decreased while aromatics increased. Sulfur was re-admitted (LPA 125 D) at a higher (than LPA 125 B) WHSV, upon which methane again increased. Finally, (LPA 125 E) upon removal of S, methane decreased and aromatics increased.

Comparison of LPA 125 D and E indicates a three fold increase in methane make in the presence sulfur.

TABLE 5
EFFECT OF $H_2S$ ON $ThO_2/Al_2O_3$/HZSM-5(c) SYNGAS CONVERSION ACTIVITY
($H_2/CO = 1$)

| Run LPA 125 - | A | B | C | D | E |
|---|---|---|---|---|---|
| | | + 2% $H_2S$ | | + 2% $H_2S$ | |
| Reaction Conditions | | | | | |
| Temperature, °F. | ← | | 800 | | → |
| Pressure, psig | ← | | 1200 | | → |
| WHSV $hr^{-1(a)}$ | 1.1 | 0.42 | 1.4 | 0.9 | 0.9 |
| Time on stream hr | 21 | 27½ | 93½ | 113 | 136½ |
| Conversion, % | | | | | |
| CO | 16.6 | 19.9 | 15.4 | 17.8 | 16.7 |
| $H_2$ | 15.8 | 15.4 | 13.9 | 17.8 | 13.5 |
| Total Effluent, wt % | | | | | |
| Hydrocarbons | 3.7 | 7.0 | 4.5 | 6.1 | 6.2 |
| $H_2O$ | 0.8 | 2.3 | 1.2 | 1.5 | 0.6 |
| $CO_2$ | 12.0 | 10.3 | 9.6 | 10.1 | 9.7 |
| CO | 77.8 | 74.7 | 79.0 | 76.7 | 77.8 |
| $H_2$ | 5.6 | 5.7 | 5.7 | 5.5 | 5.8 |
| Other(b) | 0.1 | TR | — | TR | — |
| Hydrocarbons, wt % | | | | | |
| Methane | 5.6 | 16.9 | 5.3 | 23.1 | 8.4 |
| Ethane | 21.3 | 17.3 | 11.8 | 9.2 | 12.1 |

TABLE 5-continued

EFFECT OF H$_2$S ON ThO$_2$/Al$_2$O$_3$/HZSM-5[c]
SYNGAS CONVERSION ACTIVITY
(H$_2$/CO = 1)

| Run LPA 125 - | A | B | C | D | E |
|---|---|---|---|---|---|
| Ethylene | 0.2 | 0.2 | 0.4 | 0.6 | 0.2 |
| Propane | 24.4 | 12.1 | 11.0 | 9.6 | 7.6 |
| Propylene | 0.4 | — | 0.4 | 0.2 | 0.3 |
| i-Butane | 7.5 | 2.3 | 3.5 | 4.2 | 3.0 |
| n-Butane | 4.1 | 0.5 | 1.8 | 1.3 | 1.6 |
| Butenes | — | — | — | — | — |
| C$_5$+ PON | 1.9 | 0.1 | 1.7 | 1.1 | 1.4 |
| Aromatis | 34.6 | 50.6 | 64.2 | 50.8 | 65.5 |

[a]Based on ThO$_2$/Al$_2$O$_3$ component
[b]Oxygenates or COS
[c]40/10/50 parts by weight

EXAMPLE 4

Synthesis gas containing ~2.5% H$_2$S was converted to aromatic hydrocarbons over HfO$_2$/HZSM-5. The catalyst was found to be resistant to sulfur poisoning. This is demonstrated in the attached Table 6.

Sulfur (2.5% H$_2$S) was added to the syngas (synthesis gas) feed (LPA 130B). The results clearly demonstrate the ability of the catalyst to function in the presence of sulfur. As previously observed with ThO$_2$/HZSM-5 catalysts, the presence of sulfur tends to increase methane slightly with a subsequent decrease in aromatics.

A catalyst containing 35% TiO$_2$/65% HZSM-5 gives a conversion of syngas about ⅓ of that achieved with ZrO$_2$ and about ½ of that achieved with HfO$_2$. Part of this lower conversion result is attributed to the lower TiO$_2$ content (35%). This TiO$_2$ data is shown in the attached table.

An experiment in which 0.5 wt.% of rare earth elements added to ZrO$_2$/HZSM-5 as a promoter is also shown in the attached table. The rare earth was added as the chloride salt.

TABLE 6

SYNGAS CONVERSION, ACTIVITY OF OXIDE CATALYSTS
WITH HZSM-5
(H$_2$/CO = 1)

| Run No. LPA | 130A | 130B | 128A | 126A |
|---|---|---|---|---|
| CATALYST | 50% HfO$_2$ 50% HZSM-5 | 50% HfO$_2$ 50% HZSM-5 | 35% TiO$_2$ 65% HZSM-5 | 50% ZrO$_2$/50% HZSM-5 + 0.5% Rare Earth Mix |
| H$_2$S in Feed (2.5 wt. %) | No | Yes | No | No |
| Reaction Conditions | | | | |
| Temperature, °F. | 800 | 800 | 800 | 800 |
| Pressure, psig | 1200 | 1200 | 1200 | 1200 |
| WHSV hr$^{-1}$ | 0.56 | 0.55 | 1.19 | 0.53 |
| Time on Stream, hr. | 73¾ | 98 | 21 | 21 |
| Conversion, wt. % | | | | |
| CO | 7.7 | 12.3 | 3.3 | 13.0 |
| H$_2$ | 7.6 | 12.2 | 3.8 | 11.2 |
| Total Effluent, Wt. % | | | | |
| Hydrocarbons | 3.1 | 4.0 | 1.3 | 4.5 |
| H$_2$O | 1.1 | 0.5 | Tr | Tr |
| CO$_2$ | 3.4 | 7.8 | 2.0 | 8.4 |
| CO | 86.2 | 81.8 | 90.3 | 81.2 |
| H$_2$ | 6.2 | 5.8 | 6.4 | 5.9 |
| Other | — | 0.1 | — | — |
| Hydrocarbons, Wt. % | | | | |
| Methane | 4.0 | 30.7 | 5.3 | 7.1 |
| Ethane | 14.3 | 15.6 | 36.2 | 31.6 |
| Ethylene | — | 0.1 | — | 0.1 |
| Propane | 8.2 | 16.6 | 20.4 | 20.5 |
| Propylene | — | — | — | — |
| i-Butane | 0.8 | 1.2 | 1.9 | 2.9 |
| n-Butane | 0.7 | 0.6 | 1.9 | 1.7 |
| C$_5$+ PON | 0.3 | 0.3 | 0.7 | 0.5 |
| Aromatics | 71.7 | 34.9 | 33.6 | 35.6 |

EXAMPLE 5

Initial experiments were performed with a catalyst consisting of an intimate mixture of equal parts by weight of V$_2$O$_5$ and HZSM-5. The catalyst was pre-sulfided with H$_2$S prior to testing. Results are given in Table 7.

TABLE 7

SYNGAS CONVERSION OVER VS$_x$/ZSM-5
H$_2$/CO = 1, 1200 PSIG, 800° F.

| Run No. LPA- | 131A | 131B | 131C | 131D | 131E | 131F |
|---|---|---|---|---|---|---|
| H$_2$S in feed, wt % | 2 | 0 | 0 | 0 | 1 | 0 |
| WHSV, hr$^{-1}$(a) | 2.4 | 1.6 | 1.6 | 1.6 | 1.6 | 1.7 |
| TOS, hr | 21 | 45 | 69 | 165 | 185 | 281 |
| Conversion, % | | | | | | |
| CO | 58 | 24 | 20 | 15 | 40 | 7 |
| H$_2$ | 66 | 28 | 23 | 17 | 46 | 7 |
| Reactor effluent, wt % | | | | | | |

TABLE 7-continued

SYNGAS CONVERSION OVER VS$_x$/ZSM-5
H$_2$/CO = 1, 1200 PSIG, 800° F.

| Run No. LPA- | 131A | 131B | 131C | 131D | 131E | 131F |
|---|---|---|---|---|---|---|
| Hydrocarbons | 20.1 | 1.9 | 6.3 | 4.4 | 14.2 | 2.2 |
| H$_2$O | 1.5 | 1.3 | 1.3 | 1.4 | 2.8 | 0.1 |
| CO$_2$ | 37.1 | 13.5 | 12.4 | 9.1 | 23.3 | 4.6 |
| H$_2$ | 2.3 | 4.8 | 5.1 | 5.6 | 3.6 | 6.2 |
| CO | 38.3 | 71.3 | 74.8 | 79.5 | 55.9 | 86.9 |
| Other(b) | 0.7 | — | — | — | — | — |
| Hydrocarbons, wt % | | | | | | |
| C$_1$ | 84.7 | 37.7 | 24.9 | 25.1 | 75.1 | 41.6 |
| C$_2$ | 12.8 | 20.2 | 22.9 | 21.7 | 17.9 | 34.4 |
| C$_2$= | — | 0.1 | 0.1 | 0.1 | 0.1 | — |
| C$_3$ | 2.1 | 13.3 | 17.1 | 14.1 | 5.2 | 14.4 |
| C$_3$= | — | 0.1 | 0.1 | 0.1 | — | — |
| iC$_4$ | 0.2 | 2.8 | 3.4 | 4.3 | 1.1 | 4.0 |
| nC$_4$ | 0.1 | 1.6 | 1.8 | 2.4 | 0.6 | 2.0 |
| C$_4$= | — | — | — | — | — | — |
| C$_5$+ PON | — | 1.1 | 1.4 | 2.5 | 0.1 | 3.5 |
| Aromatics | — | 23.1 | 28.4 | 29.9 | — | tr |

(a)Based on vanadia.
(b)Mainly COS.

In Run LPA 131A, syngas containing 2% H$_2$S (~6000 grains S/MSCF) was converted largely to CH$_4$, at 58% CO conversion. The catalyst is seen also to promote the shift reaction. Upon removal of H$_2$S (LPA 131B to D) an immediate drop in activity and methane selectivity occurred (despite lower space velocity) and continued to decline while ZSM-5 aromatization function became evident. After 156 hours on stream, 1% H$_2$S was re-introduced (LPA 131E) causing a substantial increase in methanation activity and selectivity. After 185 hours, H$_2$S was again removed and the catalyst allowed to de-activate. After 281 hours, conversion had dropped to 7% and ZSM-5 activity was virtually nil.

EXAMPLE 6

It was subsequently found that the ZSM-5 component was not essential for methanation activity. Experiments using bulk vanadia catalysts showed similar methanation behavior in the presence (and absence) of H$_2$S. These results are summarized in Table 8, where the activation by H$_2$S was again observed.

Bulk vanadia—by this is meant 100 percent vanadium oxide used alone in the absence of a matrix support.

TABLE 8

METHANATION OVER BULK VANADIUM CATALYST
H$_2$/CO = 1, 1200 PSIG, 800° F.

| Catalyst | V$_2$O$_5$ | VS$_x$ | | | |
|---|---|---|---|---|---|
| Run No. LPA- | 142B | 140A | 140D | 140E | 140G |
| H$_2$S in feed, wt % | 0 | 1.3 | 0 | 0 | 1.4 |
| WHSV, hr$^{-1}$ | 1.6 | 1.4 | 1.7 | 1.7 | 1.3 |
| TOS, hr | 26 | 19 | 47 | 68 | 92 |
| Conversion, wt % | | | | | |
| CO | 9 | 46 | 29 | 18 | 42 |
| H$_2$ | 15 | 39 | 29 | 22 | 56 |
| Reactor effluent, wt % | | | | | |
| Hydrocarbons | 3.8 | 12.1 | 6.1 | 5.1 | 13.5 |
| H$_2$O | 0.4 | 4.8 | 3.2 | 0.9 | 1.6 |
| CO$_2$ | 5.9 | 28.5 | 19.8 | 11.9 | 27.4 |
| H$_2$ | 5.7 | 3.9 | 4.7 | 5.2 | 3.0 |
| CO | 84.2 | 47.8 | 66.2 | 76.9 | 54.0 |
| Other(a) | — | 0.6 | — | — | 0.5 |
| Hydrocabons, wt % | | | | | |
| C$_1$ | 79.4 | 83.2 | 76.0 | 79.0 | 74.5 |
| C$_2$ | 12.7 | 15.2 | 14.1 | 11.3 | 22.8 |
| C$_2$= | 0.1 | 0.1 | tr | 0.1 | 0.2 |
| C$_3$ | 5.6 | 1.5 | 6.3 | 5.6 | 2.5 |
| C$_3$= | 0.2 | tr | 0.4 | 0.4 | tr |

TABLE 8-continued

METHANATION OVER BULK VANADIUM CATALYST
H$_2$/CO = 1, 1200 PSIG, 800° F.

| Catalyst | V$_2$O$_5$ | VS$_x$ | | | |
|---|---|---|---|---|---|
| Run No. LPA- | 142B | 140A | 140D | 140E | 140G |
| iC$_4$ | 1.7 | — | 2.4 | 2.6 | tr |
| nC$_4$ | 0.3 | — | 0.7 | 0.7 | — |
| C$_4$= | — | — | — | — | — |
| C$_5$+ | tr | — | tr | 0.3 | — |

(a)MAINLY COS.

EXAMPLE 7

Experiments with commercial supported vanadium catalysts are shown in Table 9. These data, obtained at higher space velocities (based on metal oxide) and lower H$_2$S concentration suggest that the supported catalysts are more active than the bulk materials previously examined. An interesting shift in selectivity occurred in Runs LPA 144 A-D, where it is seen that addition of molybdena to the vanadium catalyst caused a marked increase to ethane production.

TABLE 9

METHANATION OVER SUPPORTED
VANADIUM CATALYSTS
H$_2$/CO = 1, 1200 PSIG,
800° F., 3.5 WHSV(a)

| Catalyst | (10% V$_2$O$_5$ on Al$_2$O$_3$) | | | (5% V$_2$O$_3$, 5% MoO$_3$ on Al$_2$O$_3$) | | |
|---|---|---|---|---|---|---|
| Run No. LPA- | 145A | 145C | 145D | 144A | 144C | 144D |
| H$_2$S in feed, wt % | 0.5 | 0 | 0.4 | 0.6 | 0 | 0.6 |
| TOS, hr | 19 | 40 | 44 | 22 | 93 | 117 |
| Conversion, % | | | | | | |
| CO | 55 | 32 | 54 | 29 | 14 | 20 |
| H$_2$ | 60 | 32 | 56 | 36 | 18 | 29 |
| Reactor effluent, wt % | | | | | | |
| Hydrocarbons | 16.0 | 8.6 | 17.1 | 9.4 | 3.6 | 7.2 |
| H$_2$O | 2.9 | 0.7 | 2.7 | 0.8 | 1.1 | 0.6 |
| CO$_2$ | 35.7 | 22.5 | 34.0 | 19.0 | 9.8 | 12.9 |
| H$_2$ | 2.7 | 4.5 | 2.9 | 4.2 | 5.5 | 4.7 |
| CO | 42.2 | 63.6 | 42.5 | 66.2 | 80.1 | 74.3 |
| Other(b) | 0.5 | — | 0.8 | 0.4 | — | 0.3 |
| Hydrocarbons, wt % | | | | | | |
| C$_1$ | 78.5 | 88.0 | 77.5 | 52.3 | 42.9 | 44.6 |
| C$_2$ | 19.6 | 8.7 | 19.3 | 40.2 | 42.2 | 42.4 |
| C$_2$= | 0.1 | — | 0.1 | — | 0.1 | — |
| C$_3$ | 1.8 | 2.7 | 3.0 | 7.1 | 13.2 | 12.3 |
| C$_3$= | — | — | — | — | 0.1 | — |
| iC$_4$ | — | 0.4 | — | tr | 0.3 | 0.2 |
| nC$_4$ | 0.1 | 0.2 | 0.1 | 0.3 | 1.2 | 0.5 |
| C$_4$= | — | — | — | — | — | — |
| C$_5$+ | — | — | — | — | — | — |

(a)Based on metal oxide content.
(b)Mainly COS.

EXAMPLE 8

Syngas containing varying concentrations of H$_2$S was methanated over bulk vanadia. Data shown in Table 10 demonstrate a linear increase in syngas conversion with H$_2$S concentration (0–4.2%). Selectivity to hydrocarbon is higher in the presence of H$_2$S.

TABLE 10

EFFECT OF H$_2$S CONCENTRATION OF SYNGAS
METHANATION OVER BULK VANADIA
H$_2$/CO = 1, 1200 PSIG, 800° F.

| Run No. LPA- | 142A | 140H | 140G | 140F |
|---|---|---|---|---|
| H$_2$S in feed, wt % | 0 | 0.7 | 1.3 | 4.2 |
| WHSV, hr$^{-1}$ | 0.9 | 1.1 | 1.3 | 1.3 |
| TOS, hr. | 5 | 96 | 93 | 88 |
| Conversion, % | | | | |

TABLE 10-continued
EFFECT OF H₂S CONCENTRATION OF SYNGAS METHANATION OVER BULK VANADIA
$H_2/CO = 1$, 1200 PSIG, 800° F.

| Run No. LPA- | 142A | 140H | 140G | 140F |
|---|---|---|---|---|
| CO | 36 | 39 | 42 | 60 |
| $H_2$ | 37 | 47 | 56 | 60 |
| Reactor effluent, wt %(a) | | | | |
| Hydrocarbons | 7.9 | 12.4 | 13.5 | 19.9 |
| $H_2O$ | 1.8 | 2.2 | 1.6 | 2.0 |
| $CO_2$ | 25.5 | 24.2 | 27.4 | 37.7 |
| $H_2$ | 4.3 | 3.5 | 3.0 | 2.0 |
| CO | 60.6 | 57.4 | 54.0 | 37.5 |
| COS | — | 0.3 | 0.5 | 0.9 |
| Hydrocarbons, wt % | | | | |
| $C_1$ | 76.6 | 69.1 | 74.5 | 78.7 |
| $C_2$ | 13.3 | 27.1 | 22.8 | 19.5 |
| $C_2=$ | — | 0.3 | 0.2 | 0.1 |
| $C_3$ | 6.8 | 3.2 | 2.5 | 1.7 |
| $C_3=$ | — | 0.1 | tr | — |
| $iC_4$ | 2.6 | 0.2 | — | — |
| $nC_4$ | 0.6 | — | tr | — |
| $C_4$ | — | — | — | — |
| $C_5^+$ | 0.2 | — | — | — |
| Selectivity, %(b) | 46.2 | 58.7 | 57.6 | 59.4 |

(a)$H_2S$ - free basis
(b)Carbon selectivity = [ΣC in HC/ΣC in (HC + $CO_2$)] X100

The influence of the crystalline zeolite in the catalyst composition upon the products obtained in reducing carbon monoxide is evident from the following examples.

EXAMPLE 9

Thoria was prepared according to the method of Pichler and Ziesecke, as described in "The Isosynthesis," U.S. Bureau of Mines Bulletin, 488 (1950), which involved essentially the precipitation of $Th(NO_3)_4$ solutions with $Na_2CO_3$ solutions followed by filtration, washing and drying at 100° C.

A composite catalyst was prepared by ball-milling equal weights of $NH_4ZSM$-5 and dried thoria gel, pelleting and calcining at 1000° F. for 10 hours. Three experiments were done, each one at 800° F., 1215 psia, and with a mxiture of hydrogen and carbon monoxide having a $H_2/CO$ ratio of 1.0. The first and second runs involved the thorium oxide and HZSM-5, each used separately, while the third run employed a heterogeneous catalyst containing both thorium oxide and HZSM-5.

The results are summarized in Table 11.

TABLE 11

| Catalyst | (A) ThO₂ Alone | (B) HZSM-5 Alone | (C) ThO₂ plus HZSM-5 Composite |
|---|---|---|---|
| Contact Time - seconds (at reaction conditions) | 15 | 15 | 15 |
| Conversion, wt % | | | |
| CO | 5.3 | <1 | 22.4 |
| $H_2$ | 2.6 | <1 | 15.2 |
| Wt. % Hydrocarbons in total reaction effluent | 0.6 | 0.2 | 5.5 |
| Hydrocarbon Distribution (wt. %) | | | |
| Methane | 41.0 | 39.6 | 17.3 |
| $C_2$—$C_4$ hydrocarbons | 58.6 | 60.4 | 73.8 |
| $C_5^+$ | 0.4 | — | 8.9 |
| | 100.0 | 100.0 | 100.0 |
| Aromatics in $C_5^+$, wt. % | Trace | Trace | 41.6 |

EXAMPLE 10

The catalyst in this example was an intimate mixture of 50% thoria and 50% rare-earth-exchanged zeolite Y (faujasite). Synthesis gas ($H_2/CO=1$) was reacted over said catalyst at 800° F., 1215 psig and 15 seconds contact time, giving the following conversion and products shown in Table 12.

TABLE 12

| Catalyst | ThO₂ + REY |
|---|---|
| Contact Time - seconds (at reaction conditions) | 15 |
| Conversion, wt. % | |
| CO | 5.3 |
| $H_2$ | 2.9 |
| Wt. % Hydrocarbons in total reaction effluent | 0.8 |
| Hydrocarbon Distribution (wt. %) | |
| Methane | 42.8 |
| $C_2$-$C_4$ hydrocarbons | 54.7 |
| $C_5^+$ | 2.5 |
| Aromatics in $C_5^+$, wt. % | 68.0 |

EXAMPLE 11

The open literature appears to contain no references to the methanation of syngas containing relatively large amounts, at least about 5000 ppm of sulfur. Published information discusses the effects obtained with low sulfur concentration comprising less than about 0.5 percent sulfur. The methanation of sulfur containing syngas of larger sulfur concentrations is presented in the table below employing a Cr/Al/ZSM-5 catalyst with and without sulfur present and a Co/Mo/Al₂O₃ catalyst at higher sulfur concentration than the prior art.

TABLE 13
SYNGAS METHANATION
$H_2/CO = 1$, 1200 PSIG, 800° F.

| Catalyst | Cr/Al/ZSM-5 | Cr/Al/ZSM-5 | Co/Mo/Al₂O₃ |
|---|---|---|---|
| Run No. LPA- | 129C | 129D | 145A |
| $H_2S$ in feed, wt % | 0 | 0.6 | 0.7 |
| WHSV, hr⁻¹(a) | 4 | 4 | 5 |
| Conversion, % | | | |
| CO | 7 | 10 | 75 |
| $H_2$ | 7 | 11 | 79 |
| Hydrocarbon Product, wt % | | | |
| Methane | 6.8 | 81.1 | 50.7 |
| Ethane | 31.9 | 13.7 | 44.0 |
| Ethylene | — | — | — |
| Propane | 14.8 | 4.4 | 5.1 |
| Propylene | — | — | — |
| Butanes | 2.0 | 0.8 | 0.2 |
| Butenes | — | — | — |
| $C_5^+$ PON | 0.3 | tr | — |
| Aromatics | 44.2 | — | — |

(a)Based on metal oxide component.

It will be observed that at the operating conditions of about 800° F. and 1200 psig fuel gas of high methane and ethane content is particularly produced with the catalyst free of an aromatizing catalyst component such as the special class of crystalline zeolites represented by ZSM-5 crystalline zeolite. On the other hand, the Cr/Al/ZSM-5 catalyst composition produced high yields of methane and considerable ethane when the feed contained a significant amount of sulfur in the form of hydrogen sulfide. Thus, the chromium catalyst being a sulfur tolerant composition, regenerable by a hydrogen rich atmosphere substantially free of sulfur or regenerable with an oxygen containing gas, can be relied upon to produce a substantially different product substantially as desired and comprising a high BTU fuel gas in one operating mode and a methane rich gaseous product of lower ethane content in another operating mode. It will be further observed that the conversion of syngas is much higher for the Co/Mo catalyst than the Cr/Al catalyst at the same operating conditions and the yield of ethane is higher with the molybdenia containing catalyst.

heating value of ethane is about 1786 BTU/cu. ft. while that of methane is 1012 BTU/cu. ft. It will be observed from the data presented in the table below that these molybdenia containing catalysts were all producers of fuel gas rich in methane and ethane. It will also be observed that the presence of hydrogen sulfide in the syngas tended to suppress the formation of propane.

TABLE 14

Conversion of Synthesis Gas
$H_2/CO = 1$, $P = 1200$ psig, $T = 800°$ F.

| Catalyst | 10% $MoO_3$ on $Al_2O_3$ | | 10% $MoO_3$ + 1%K on $Al_2O_3$ | | 2.9% $CoO_3$, 9.1% $MoO_3$ 4% $SiO_2$ on $Al_2O_3$ | | | | | 5%$V_2O_2$, %5$MoO_3$ on $Al_2O_3$ | |
|---|---|---|---|---|---|---|---|---|---|---|---|
| Run LPA | 149B | 149C | 150A | 150B | 146B | 146A | 146C | 146E | 146G | 144C | 144D |
| $H_2S$ in feed, wt. % | 0 | 1.6 | 0 | 1.6 | 0 | 0.7 | 0 | 0.6 | 0 | 0 | 0.6 |
| Space velocity, hr$^{-1}$(a) | 6 | 7 | 7 | 6 | 6 | 7 | 7 | 8 | 6 | 7 | 7 |
| Conversion, % | | | | | | | | | | | |
| CO | 75 | 81 | 71 | 79 | 81 | 75 | 83 | 68 | 74 | 14 | 20 |
| $H_2$ | 80 | 85 | 77 | 85 | 85 | 79 | 86 | 74 | 79 | 18 | 29 |
| Product $CO_2/H_2O$ | 5.8 | 16.7 | 5.7 | 8.9 | 13.4 | 7.4 | 15.6 | 10.7 | 6.6 | 8.9 | 21.5 |
| Hydrocarbons, wt. % | | | | | | | | | | | |
| Methane | 61.5 | 74.9 | 52.9 | 71.7 | 45.6 | 50.7 | 52.1 | 49.4 | 57.3 | 42.9 | 44.6 |
| Ethane | 29.1 | 22.9 | 35.2 | 25.6 | 43.8 | 44.0 | 43.2 | 45.3 | 42.4 | 42.3(b) | 42.4 |
| Propane | 7.5 | 2.2 | 9.4 | 2.6 | 8.4 | 5.1 | 4.4 | 5.0 | 6.0 | 13.3(c) | 12.3 |
| $C_4$+ | 1.9 | — | 2.7 | 0.1 | 2.3 | 0.4 | 0.3 | 0.3 | 0.3 | 1.5 | 0.7 |

(a)weight feed/weight $MoO_3$ × hr.
(b)0.1% ethylene
(c)0.1% propylene

EXAMPLE 12

The influence of molybdenia on the heating value of fuel gas produced from syngas was further studied with a variety of catalysts comprising Mo/Al$_2$O$_3$; Co/Mo/Si/Al$_2$O$_3$; and V/Mo/Al$_2$O$_3$. The methanation of syngas containing substantial quantities of hydrogen sulfide (H$_2$S) was achieved with catalyst containing molybdenia as a major and a minor component of the catalyst. Thus the molybdenia catalyst above identified produced under elevated temperature conditions within the range of 700° to 1500° F. at a pressure within the range of 20 to 100 atmospheres, a feed gas product rich in methane and comprising substantial concentrations of ethane. Ethane is a desirable component in fuel gas since it increases the heating value of the fuel gas. The (gross)

Having thus generally described the present invention and specifically discussed examples in support thereof, it is to be understood that no undue restrictions are to be imposed by reasons thereof except as defined by the following claims.

We claim:

1. In a process for converting synthesis gas comprising carbon monoxide and hydrogen to gases rich in methane and increased ethane which comprises, contacting synthesis gas at a temperature in the range of 700° to 1500° F. and pressure in the range of 20 to 100 atmospheres in the presence of a sulfur reactant material with a catalyst comprising vanadium and molybdenum on an alumina support material and recovering a high BTU product gas rich in methane and ethane.

* * * * *

UNITED STATES PATENT AND TRADEMARK OFFICE
CERTIFICATE OF CORRECTION

PATENT NO. : 4,177,202
DATED : December 4, 1979
INVENTOR(S) : CLARENCE D. CHANG and WILLIAM H. LANG It is certified that error appears in the above—identified patent and that said Letters Patent are hereby corrected as shown below:

Column 1, Line 64 - "in" should read -- is --

Column 17, Line 5 in Table 7 - "1.9" should read -- 9.1 --

Signed and Sealed this

Eighth Day of July 1980

[SEAL]

Attest:

SIDNEY A. DIAMOND

Attesting Officer — Commissioner of Patents and Trademarks